United States Patent
Igarashi

(10) Patent No.: US 11,119,306 B2
(45) Date of Patent: Sep. 14, 2021

(54) IMAGE PICKUP OPTICAL SYSTEM, ENDOSCOPE, AND IMAGE PICKUP APPARATUS

(71) Applicant: OLYMPUS CORPORATION, Hachioji (JP)

(72) Inventor: Tsutomu Igarashi, Hachioji (JP)

(73) Assignee: OLYMPUS CORPORATION, Tokyo (JP)

(*) Notice: Subject to any disclaimer, the term of this patent is extended or adjusted under 35 U.S.C. 154(b) by 0 days.

(21) Appl. No.: 16/920,329

(22) Filed: Jul. 2, 2020

(65) Prior Publication Data

US 2020/0333580 A1 Oct. 22, 2020

Related U.S. Application Data

(63) Continuation of application No. PCT/JP2018/032387, filed on Aug. 31, 2018.

(30) Foreign Application Priority Data

Feb. 9, 2018 (JP) .............................. JP2018-022489

(51) Int. Cl.
  *G02B 23/24* (2006.01)
  *A61B 1/05* (2006.01)

(52) U.S. Cl.
  CPC .............. *G02B 23/243* (2013.01); *A61B 1/05* (2013.01); *G02B 23/2484* (2013.01)

(58) Field of Classification Search
  CPC .............. G02B 23/243; G02B 23/2484; G02B 23/2469; G02B 5/005; G02B 13/04;
  (Continued)

(56) References Cited

U.S. PATENT DOCUMENTS

2012/0293641 A1* 11/2012 Nagamizu .......... A61B 1/00096
  348/65
2016/0007833 A1* 1/2016 Huang ................. A61B 1/0008
  600/109

FOREIGN PATENT DOCUMENTS

JP   H03275028 A   12/1991
JP   H10258058 A    9/1998
(Continued)

OTHER PUBLICATIONS

International Preliminary Report on Patentability (IPRP) (and English translation thereof) dated Aug. 20, 2020 issued in counterpart International Application No. PCT/JP2018/032387.
(Continued)

*Primary Examiner* — Jared Walker
(74) *Attorney, Agent, or Firm* — Holtz, Holtz & Volek PC

(57) ABSTRACT

An image pickup optical system includes an image pickup field of view in which part of an endoscope is reflected, an aperture stop and a peripheral light reduction stop. The peripheral light reduction stop is positioned in an optical axis direction satisfying Conditional Expression (1), in the peripheral light reduction stop, when a side on which part of the endoscope exists in the image pickup field of view is a first direction and a side on which no part of the endoscope exists in the image pickup field of view is a second direction, an opening portion of the peripheral light reduction stop satisfies Conditional Expression (2), and a peripheral light reduction quantity in the second direction is smaller than a peripheral light reduction quantity in the first direction by shielding no effective luminous flux in the second direction or reducing shielding quantity of the effective luminous flux, $$0.5 < |Hch/Haxm| < 5 \qquad (1),$$

$$-1.2 < (La - |Hch|)/|Haxm| < 0.6 \qquad (2).$$

20 Claims, 10 Drawing Sheets

(58) Field of Classification Search
CPC .......... G02B 13/00; G02B 23/26; A61B 1/05;
A61B 1/042; A61B 1/018; A61B 1/07;
A61B 1/00188; A61B 8/12; A61B 8/14
See application file for complete search history.

(56) References Cited

FOREIGN PATENT DOCUMENTS

| | | |
|---|---|---|
| JP | 2009017964 A | 1/2009 |
| JP | 2016129576 A | 7/2016 |

OTHER PUBLICATIONS

International Search Report (ISR) (and its English-language translation) dated Nov. 27, 2018 issued in International Application No. PCT/JP2018/032387.
Written Opinion dated Nov. 27, 2018 issued in International Application No. PCT/JP2018/032387.

\* cited by examiner

DOWN SIDE

IMAGE PICKUP OPTICAL SYSTEM, ENDOSCOPE, AND IMAGE PICKUP APPARATUS

CROSS-REFERENCE TO RELATED APPLICATION

The present application is a continuation application of PCT/JP2018/032387 filed on Aug. 31, 2018 which is based upon and claims the benefit of priority from Japanese Patent Application No. 2018-022489 filed on Feb. 9, 2018; the entire contents of which are incorporated herein by reference.

BACKGROUND

Technical Field

The present disclosure relates to an endoscope image pickup optical system, mainly an image pickup optical system of a medical ultrasonic endoscope, and an endoscope and Image pickup apparatus.

Description of the Related Art

Ultrasonic endoscopes are equipped with ultrasonic transducers at distal ends of insertion units of endoscopes. The insertion units are inserted into the body cavities, such as digestive organs and bronchi. In this manner, ultrasonic endoscopes perform diagnosis and/or treatment under observation of ultrasonic images.

In addition, ultrasonic endoscopes observe optical images of the target regions by being inserted into organs serving as observation targets using optical images. Like this, ultrasonic endoscopes generally generate and acquire two types of images, that is, ultrasonic images and optical images.

With an optical image acquired with ordinary visible light, surface information of the organ is acquired. However, it is impossible to acquire the deep portion of the organ. With an ultrasonic image, a tomographic image including the deep portion of the organ is acquired, and it is useful for use of extracting tissue from the deep portion of the organ. In particular, in a bronchoscope, a lymph node that is hard to recognize with an optical image is subjected to a biopsy and tissue extraction from the inside of the bronchus under an ultrasonic image, and used for diagnosis of cancer metastasis.

To acquire an ultrasonic image of the organ, ultrasonic waves are transmitted to the organ. For this reason, it is required to prevent interposition of the air between the transducer and the organ. For this reason, ultrasonic waves are transmitted to the organ by directly bringing the transducer into contact with the organ or by inserting a balloon filled with water between the transducer and the organ.

By such circumstances described above, in an ultrasonic endoscope, a transducer is generally disposed at the most distal end side of the insertion unit, as a structure enabling easy contact with the organ and a structure easily compliant with attachment of a balloon.

Accordingly, the optical system of the ultrasonic endoscope is required to be designed on the assumption that the ultrasonic transducer is disposed at the most distal end side of the insertion unit. In an ultrasonic endoscope, the optical system acquiring an optical image is generally disposed at a position receding from the transducer.

Under the constraints relating to the structure of the ultrasonic endoscope described above, an optical image is required to achieve easy observation of the insertion direction of the insertion unit and visual recognition of the region to be imaged with the ultrasonic transducer and/or the target region to be injected with a biopsy needle.

Japanese Patent Application Laid-open No. 2016-129576, Japanese Patent Application Laid-open No. 2009-17964, and Japanese Patent Application Laid-open No. H10-258058 disclose techniques relating to optical images of ultrasonic endoscopes.

SUMMARY

An image pickup optical system according to at least some embodiments of the present disclosure is an image pickup optical system including an image pickup field of view in which part of an endoscope is reflected, the image pickup optical system includes:
an aperture stop; and
a peripheral light reduction stop, wherein
the peripheral light reduction stop is disposed in a position in an optical axis direction satisfying the following Conditional Expression (1),
in the peripheral light reduction stop, when a side on which the part of the endoscope exists in the image pickup field of view is a first direction and a side on which no part of the endoscope exists in the image pickup field of view is a second direction,
an opening portion of the peripheral light reduction stop satisfies the following Conditional Expression (2), and
a peripheral light reduction quantity in the second direction is smaller than a peripheral light reduction quantity in the first direction by shielding no effective luminous flux in the second direction or reducing shielding quantity of the effective luminous flux:

$$0.5 < |Hch/Haxm| < 5 \qquad (1)$$

$$-1.2 < (La - |Hch|)/|Haxm| < 0.6 \qquad (2)$$

where
Hch is a chief ray height of image height in the first direction at the position of the peripheral light reduction stop,
Haxm is an on-axis marginal beam height at the position of the peripheral light reduction stop, and
La is a distance from an optical axis to an opening end in the first direction of the peripheral light reduction stop.

In addition, an endoscope according to at least some embodiments of the present disclosure is an endoscope includes an image pickup optical system, wherein the image pickup optical system includes:
an image pickup field of view in which part of the endoscope is reflected;
an aperture stop; and
a peripheral light reduction stop,
the peripheral light reduction stop is disposed in a position in an optical axis direction satisfying the following Conditional Expression (1),
in the peripheral light reduction stop, when a side on which the part of the endoscope exists in the image pickup field of view is a first direction and a side on which no part of the endoscope exists in the image pickup field of view is a second direction,
an opening portion of the peripheral light reduction stop satisfies the following Conditional Expression (2), and
a peripheral light reduction quantity in the second direction is smaller than a peripheral light reduction quantity in the first direction by shielding no effective luminous flux in the second direction or reducing shielding quantity of the effective luminous flux:

$$0.5 < |Hch/Haxm| < 5 \quad (1)$$

$$-1.2 < (La - |Hch|)/|Haxm| < 0.6 \quad (2)$$

where

Hch is a chief ray height of image height in the first direction at the position of the peripheral light reduction stop, Haxm is an on-axis marginal beam height at the position of the peripheral light reduction stop, and La is a distance from an optical axis to an opening end in the first direction of the peripheral light reduction stop.

In addition, an image pickup apparatus according to at least some embodiments of the present disclosure includes the image pickup optical system described above.

DETAILED DESCRIPTION

An image pickup optical system and an endoscope and an image pickup apparatus according to embodiments will now be described hereinafter with respect to the reason why such structures are adopted and the functions thereof, with reference to drawings. The present disclosure is not limited to the following embodiments.

Hereinafter, an endoscope image pickup optical system and endoscope apparatus will be described as an embodiment of the image pickup optical system the endoscope, and the image pickup apparatus.

Embodiment A

An endoscope apparatus according to Embodiment A will now be described hereinafter on the basis of FIG. 7A, FIG. 8A, FIG. 8B, and FIG. 8C.

Figure 7A:
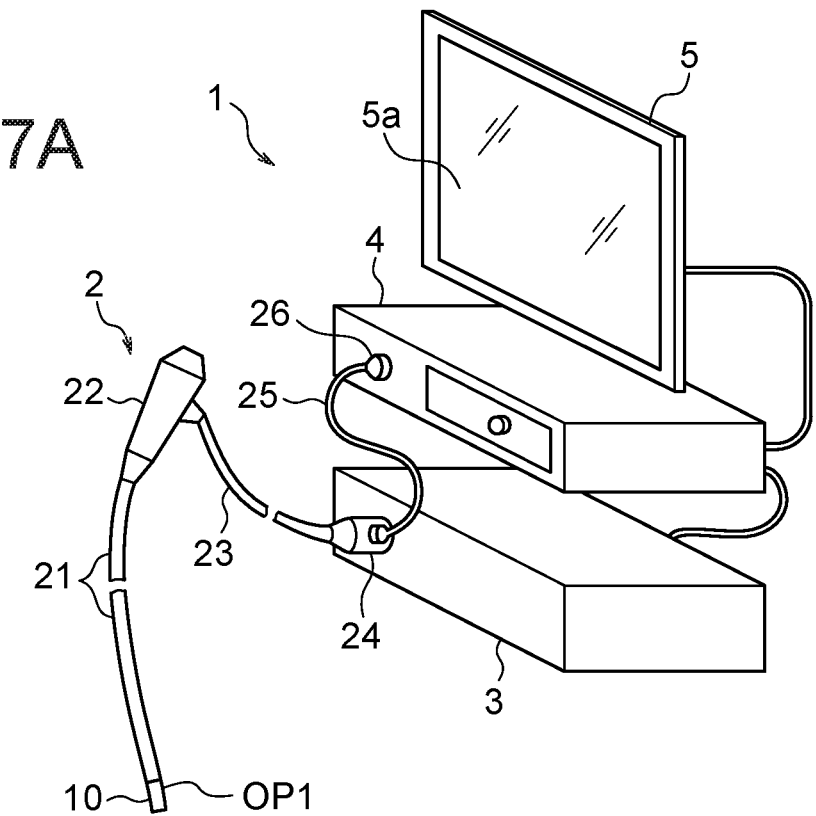
FIG. 7A is a diagram illustrating an endoscope apparatus according to Embodiment A.

FIG. 7A is a diagram illustrating the endoscope apparatus according to Embodiment A. FIG. 8A is a diagram illustrating a perspective structure of a distal end part of the endoscope apparatus according to Embodiment A, FIG. 8B is a diagram illustrating main functional shields according to Embodiment A, and FIG. 8C is a diagram illustrating a screen shape according to Embodiment A. Because the present embodiment is not related to a system configuration of the ultrasonic observation function, illustration and an explanation of the system configuration relating to the ultrasonic observation function are omitted in FIG. 7. However, because the ultrasonic transducer module is related as the subject of the optical image, the ultrasonic transducer module will be explained hereinafter with reference to FIGS. 8A, 8B and 8c.

FIG. 7A is a diagram illustrating a schematic structure of an endoscope apparatus 1 according to the present embodiment.

As illustrated in FIG. 7A, the endoscope apparatus 1 according to the present embodiment includes an electronic endoscope 2 including a solid-state image sensor IMG (see FIG. 2A) serving as an image pickup apparatus therein, a light source apparatus 3 including a light source supplying illumination light to the electronic endoscope 2, an image processing apparatus 4 executing signal processing for the solid-state image sensor IMG of the electronic endoscope 2, and a monitor 5 displaying an endoscope image formed of an image signal output via the image processing apparatus 4.

The electronic endoscope 2 includes an elongated insertion part 21 having flexibility and including the solid-state image sensor IMG therein, a thick operating part 22 formed at the rear end of the insertion part 21, a distal end rigid portion 10, and a universal cord 23 extended from a side portion of the operating part 22. A distal end of the universal cord 23 is provided with a connector part 24 detachably connectable with the light source apparatus 3. A distal end of a connection cord 25 extended on the connector part 24 side is provided with an electric connector part 26 detachably connectable with the image processing apparatus 4.

The endoscope apparatus according to Embodiment A has a video scope structure in which an image pickup optical system OP1 is disposed at the distal end of the endoscope. In this case, because the image pickup optical system OP1 directly forms a subject image on the solid-state image sensor IMG (see FIG. 1A), the image pickup optical system OP1 can also be referred to as an objective optical system. Hereinafter, the optical system forming an image on the solid-state image sensor IMG is referred to as "image pickup optical system".

FIG. 8A is a perspective view schematically illustrating a distal end structure of the insertion part of the ultrasonic endoscope according to Embodiment A. A distal end part 211 includes an ultrasonic transducer module 214 retaining an ultrasonic transducer 7, an illumination lens LL collecting illumination light and emitting the illumination light to the outside, and an endoscope module 215 forming part of an image pickup optical system and including the image pickup optical system OP1 taking light from the outside. A treatment tool projecting opening 215c is formed in the endoscope module 215. The treatment tool projecting opening 215c connects with a treatment tool insertion path formed in the insertion part 21, and causes a treatment tool to project from the distal end of the insertion part 21. The treatment tool insertion path is provided such that a portion close to the distal end connecting with the treatment tool projecting opening 215c is inclined with respect to the longitudinal axis of the insertion part 21, and the treatment tool projects from the treatment tool projecting opening 215c in a direction inclined with respect to the longitudinal axis. The longitudinal axis herein is an axis extending along the longitudinal direction of the insertion part 21.

Illumination light emitted from the illumination optical system LL is irradiated on the adjacent ultrasonic transducer 7. The light reflected and scattered from the ultrasonic transducer 7 is made incident on the image pickup optical system OP1 and imaged.

Generally, the ultrasonic transducer 7 is disposed on the "Down" side of the screen direction. For this reason, when the ultrasonic transducer 7 is reflected on the screen, the ultrasonic transducer is reflected on the "Down" side of the screen, as illustrated in FIG. 8C. The shape of the field of view is octagonal. The vertical image height IHv and the maximum image height IH of the direction of the ultrasonic transducer 7 are different. It is preferable that the relation "IHv<IH" is satisfied.

The ultrasonic transducer 7 reflected on the "Down" side of FIG. 8C is illuminated with the illumination light with high illuminance, and brightness thereof is easily saturated. For this reason, the "Down" side is set as the direction to be subjected to peripheral light reduction.

Embodiment B

An endoscope apparatus according to Embodiment B will be explained hereinafter on the basis of FIG. 7B, FIG. 9A, FIG. 9B, and FIG. 9C.

Figure 7B:
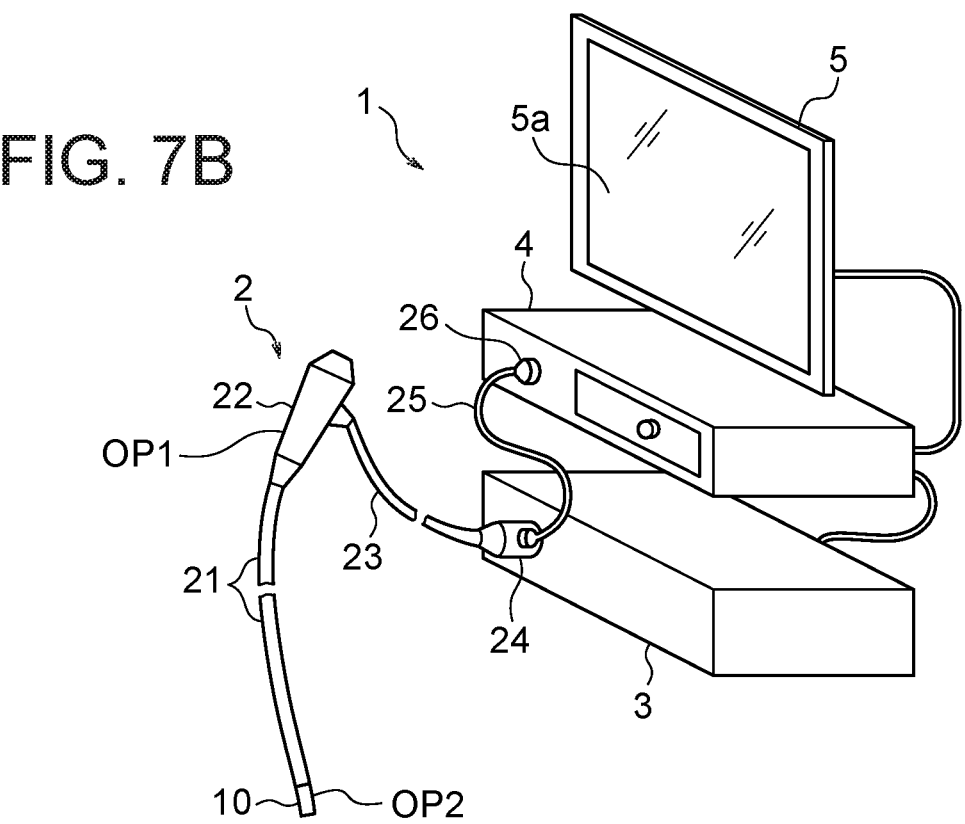
FIG. 7B is a diagram illustrating an endoscope apparatus according to Embodiment B.
Figure 8A:
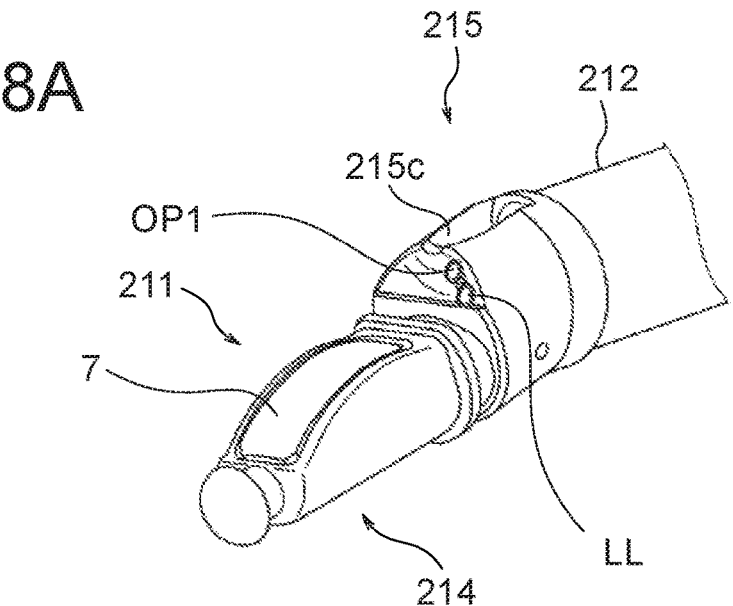
FIG. 8A is a diagram illustrating a perspective structure of a distal end part of the endoscope apparatus according to Embodiment A.
Figure 8B:
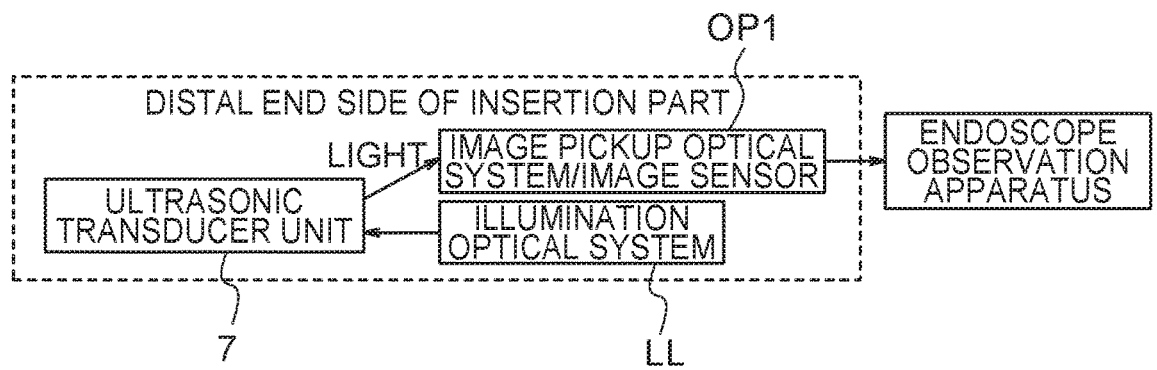
FIG. 8B is a diagram illustrating main functional shields according to Embodiment A.
Figure 8C:
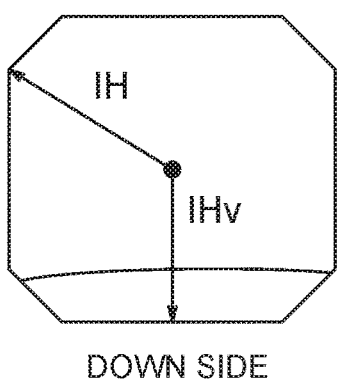
FIG. 8C is a diagram illustrating a screen shape according to Embodiment A.
Figure 9A:
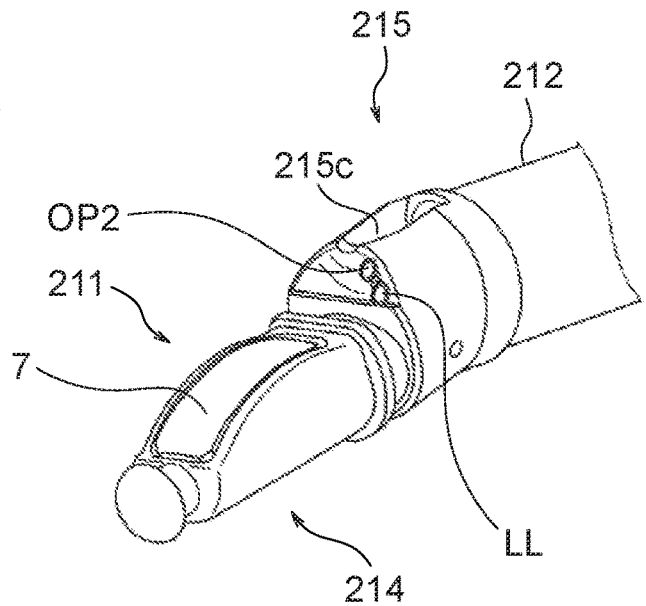
FIG. 9A is a diagram illustrating a perspective structure of a distal end part of the endoscope apparatus according to Embodiment B.
Figure 9B:
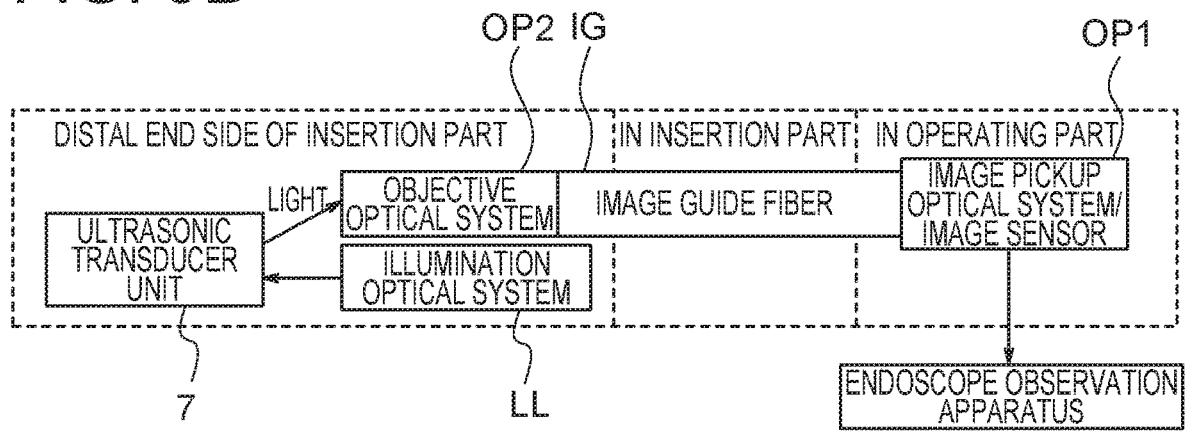
FIG. 9B is a diagram illustrating main functional shields according to Embodiment B.
Figure 9C:
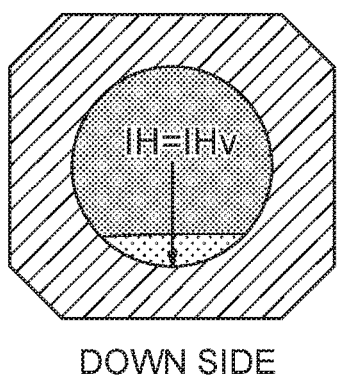
FIG. 9C is a diagram illustrating a screen shape according to Embodiment B.

FIG. 7B is a diagram illustrating an endoscope apparatus according to Embodiment B. FIG. 9A is a diagram illustrating a perspective structure of a distal end part of the endoscope apparatus according to Embodiment B, FIG. 9B is a diagram illustrating main functional shields according to Embodiment B, FIG. 9C is a diagram illustrating a screen shape according to Embodiment B. The same constituent elements as those of Embodiment A described above are denoted with the same reference numerals, and an overlapping explanation thereof is omitted.

In the endoscope apparatus according to the present embodiment, an optical image of an objective optical system OP2 is transmitted to the endoscope image pickup optical system OP1 with an image guide fiber IG (see FIG. 5A and FIG. 6A) in the insertion part 21. Specifically, the endoscope apparatus has a fiber scope structure in the insertion part 21. The endoscope has a structure in which the optical image transmitted with the image guide fiber IG is relayed to the solid-state image sensor IMG with the image pickup optical system OP1 disposed in the operating part 22.

The illumination light emitted from the illumination optical system LL is irradiated on the adjacent ultrasonic transducer 7. Thereafter, reflected and scattered light of the irradiated light from the ultrasonic transducer 7 is made incident on the objective optical system OP2 of the fiber scope structure. The incident light is transmitted with the image guide fiber IG, and imaged with the solid-state image sensor IMG.

FIG. 9A is a perspective view schematically illustrating the distal end structure of the insertion part of the ultrasonic endoscope according to Embodiment B.

The ultrasonic transducer 7 is disposed on the "Down" side of the screen direction, in the same manner as Embodiment A. Accordingly, when the ultrasonic transducer 7 is reflected in the screen, the ultrasonic transducer 7 is reflected on the "Down" side in the screen, as illustrated in FIG. 9C. As the shape of the field of view, a circular image guide fiber image is projected in an octagonal screen of the solid-state image sensor IMG like Embodiment A. For this reason, the range of the field of view has a circular shape. Because the field of view has a circular shape, the vertical image height IHv and the maximum image height IH of the direction of the ultrasonic transducer 7 are equal to each other.

In the same manner as Embodiment A, the ultrasonic transducer 7 reflected on the "Down" side of FIG. 9C is illuminated with the illumination light with high illuminance, and brightness thereof is easily saturated. For this reason, the "Down" side is set as the direction to be subjected to peripheral light reduction.

Ratio of Reflection of Ultrasonic Transducer on Image

The ratio of reflection of the ultrasonic transducer 7 on the image region will be explained hereinafter. When the quantity of reflection of the ultrasonic transducer 7 on the image region is too large, the range of the field of view on the organ side is narrowed. By contrast, when the quantity of reflection thereof is too small, it is difficult to recognize whether a contact part between the ultrasonic transducer 7 and the organ or the balloon is viewed by the observer.

Accordingly, the ratio of reflection of the ultrasonic transducer 7 to the screen size in the perpendicular direction is preferably set to fall within the range of 3% to 30%. More preferably, the ratio is set to approximately 5 to 15%. However, the ratio value is not determined only according to the optical specifications of the optical system. The layout of the ultrasonic transducer 7 and the optical system (image pickup optical system and illumination optical system) at the distal end of the endoscope greatly influences on the ratio. In addition, the layout of the optical system is greatly influenced by reduction in diameter of the endoscope. Accordingly, it is preferable that peripheral light reduction is optimized on the optical design side for such a wide range of the ratio.

Embodiments

Figure 1A:
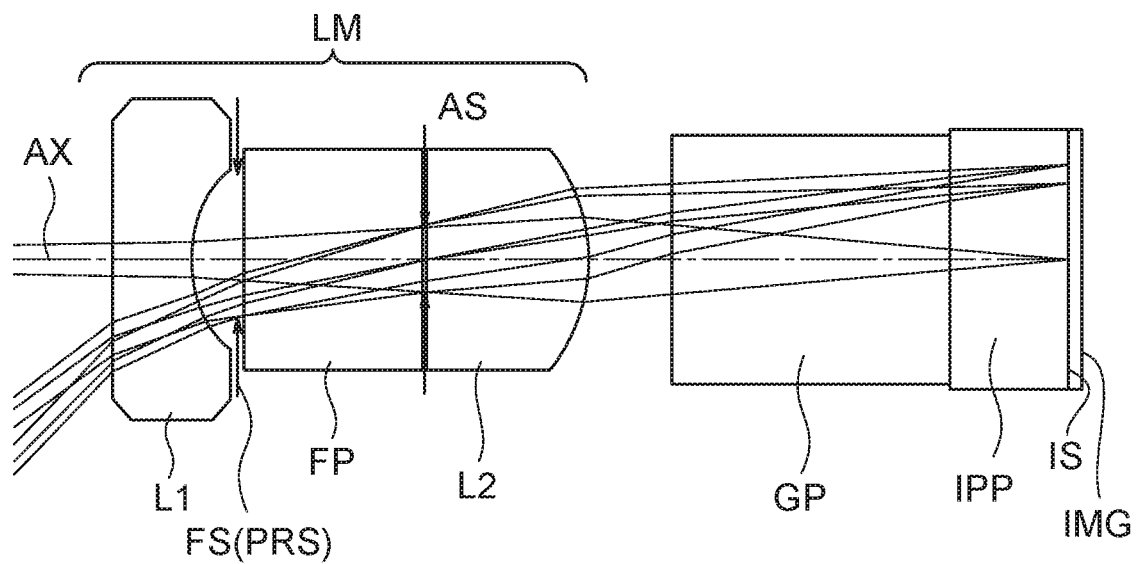
FIG. 1A is a lens cross-sectional view of an endoscope image pickup optical system according to an embodiment.
Figure 1B:
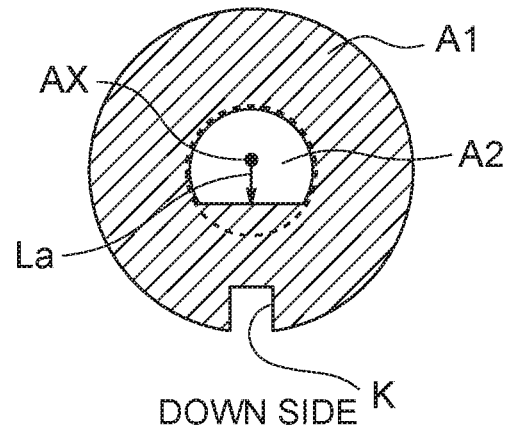
FIG. 1B is a front view of a peripheral light reduction stop according to the embodiment.

The endoscope image pickup optical system included in the endoscope described above will be explained hereinafter. FIG. 1A is a lens cross-sectional view of the endoscope image pickup optical system OP1 according to an embodiment, and FIG. 1B is a front view of a peripheral light reduction stop PRS according to the embodiment.

An endoscope image pickup optical system will be described below as an example of the image pickup optical system.

The image pickup optical system including an image pickup field of view in which part of an endoscope is reflected, the image pickup optical system includes,
an aperture stop; and
a peripheral light reduction stop, wherein
the peripheral light reduction stop is disposed in a position in an optical axis direction satisfying the following Conditional Expression (1),
in the peripheral light reduction stop, when a side on which the part of the endoscope exists in the image pickup field of view is a first direction and a side on which no part of the endoscope exists in the image pickup field of view is a second direction,
an opening portion of the peripheral light reduction stop satisfies following Conditional Expression (2), and
a peripheral light reduction quantity in the second direction is smaller than a peripheral light reduction quantity in the first direction by shielding no effective luminous flux in the second direction or reducing shielding quantity of the effective luminous flux:

$$0.5 < |Hch/Haxm| < 5 \quad (1)$$

$$-1.2 < (La - |Hch|)/|Haxm| < 0.6 \quad (2)$$

where
Hch is a chief ray height of image height in the first direction at the position of the peripheral light reduction stop,
Haxm is an on-axis marginal beam height at the position of the peripheral light reduction stop, and
La is a distance from the optical axis to an opening end in the first direction of the peripheral light reduction stop.

In the present embodiment, the "Down" luminous flux side of the peripheral light reduction stop PRS, that is, the transducer direction to be darkened is cut in a straight shape. In this manner, in an observation image, it is possible to prepare an image surface illuminance distribution in which only the direction of the ultrasonic transducer 7 in which brightness is easily saturated is reduced.

The shape of the opening portion of the peripheral light reduction stop PRS is not an ordinary circular opening, but a shape having a cut characteristic only in the specific direction, like a D-cut. In FIG. 1B, a circular dotted line indicates effective luminous flux. The hatched portion is a light shield portion A1. The opening portion is denoted by "A2".

The Conditional Expression (1) provides a ratio |Hch/Haxm| of the on-axis marginal beam height Haxm to the chief ray height Hch. In the light reduction distribution, the ratio is a condition to control the image height at which light reduction is started and to control the inclination of light reduction.

In the vicinity of the aperture stop AS with the small |Hch/Haxm|, the image height at which light reduction is started is small, and a gentle light reduction characteristic is provided. In the aperture stop AS surface, when Hch is substantially 0 and |Hch/Haxm| is 0, no illuminance distribution can be formed in the image surface.

In a place distant from the aperture stop AS and having |Hch/Haxm| with a large value, the image height at which light reduction is started is large, and a sharp light reduction characteristic is provided. In the image surface (image pickup surface) IS, Haxm is substantially 0. When |Hch/Haxm| is ∞, a sharp cut characteristic is provided like the function of a field mask, and light is shielded, not reduced.

For variety of the ratio of reflection of the ultrasonic transducer to the screen size in the perpendicular direction, by selecting the position of the peripheral light reduction stop PRS in the optical axis direction in a position satisfying the Conditional Expression (1), it is possible to optimize the peripheral light reduction characteristic.

A thin plate stop or a light shield film of an optical member can be mounted as the peripheral light reduction stop PRS.

When the ratio is smaller than the lower limit value of the Conditional Expression (1), the image height at which light reduction is started is too small. The ratio is not preferable because the effective field of view to observe the organ side is subjected to light reduction, and it is impossible to increase the light reduction characteristic of the ultrasonic transducer image due to the influence.

When the ratio is larger than the upper limit value of the Conditional Expression (1), the image height at which light reduction is started is too large. The ratio is not preferable because a portion for which light is not reduced is easily generated in the ultrasonic transducer image. It is not preferable because too sharp brightness fluctuation occurs in the ultrasonic transducer image range, and the observer has an uncomfortable feeling.

The Conditional Expression (2) provides a proper range of (La−|Hch|)/|Haxm|. It is possible to control the degree of peripheral light reduction with the value of (La−|Hch|)/|Haxm|.

The values of Hch and Haxm at the peripheral light reduction stop PRS determined in the range of the Conditional Expression (1) are determined in advance. For this reason, it suffices to determine the distance La from the optical axis AX to the opening end of the peripheral light reduction stop PRS within the range of the Conditional Expression (2).

When the opening portion A2 is cut in a straight shape with the chief ray height Hch, substantially half of the luminous flux area is cut, and it is possible to reduce the peripheral light quantity at the corresponding image height to substantially half. When "La=Hch" is satisfied, it means that the specific direction opening of the peripheral light reduction stop PRS is determined with the chief ray height. In the Conditional Expression (2), "(La−|Hch|)/|Haxm|=0" corresponds to this case.

"(La−|Hch|)/|Haxm|>0" means a cut in a position higher than the chief ray height. This is a cut smaller than half of the luminous flux area, and peripheral light reduction decreases.

"(La−|Hch|)/|Haxm|>1" is a state in which peripheral light reduction hardly occurs.

"(La−|Hch|)/|Haxm|<0" causes a cut in a position lower than the chief ray height. The cut is a cut exceeding half of the luminous flux area, and peripheral light reduction is increased.

In the case of "(La−|Hch|)/|Haxm|<−1", the peripheral light quantity is substantially 0, and strictly a vignetting of field of view occurs. However, when priority is given to reduction in diameter of the endoscope, it is required to dispose the illumination optical system and the ultrasonic transducer closer to each other, and there are the cases where increase of the degree of peripheral light reduction is required as a measure against saturation of the ultrasonic transducer. Accordingly, there are cases where the ratio is set smaller than −1.

When the value is smaller than the lower limit value of the Conditional Expression (2), the value is not preferable because the degree of peripheral light reduction is too large, and an unallowable vignetting of field of view occurs.

CL2

When the value is larger than the lower limit value of the Conditional Expression (2), the value is not preferable because the degree of peripheral light reduction is too small, and does not function as a measure against saturation of brightness.

In addition, according to a preferable aspect of the present embodiment, it is preferable that the following Conditional Expressions (3) and (4) are satisfied:

$$0.6 < Iref \quad (3)$$

$$Icut/Iref < 0.7 \quad (4)$$

where Iref is a ratio of the peripheral light quantity to the central light quantity in the image height of the first direction when the effective luminous flux is not shielded with the peripheral light reduction stop, and Icut is a ratio of the peripheral light quantity to the central light quantity in the image height of the first direction when the effective luminous flux is shielded with the peripheral light reduction stop.

The Conditional Expression (3) provides the proper range of Iref.

In the endoscope image pickup optical system, the peripheral light quantity ratio generally fluctuates according to factors other than the peripheral light reduction stop PRS. For example, peripheral light quantity fluctuations are caused by vignetting caused by cutting of harmful light of the flare stop FS, and peripheral light quantity fluctuations is caused by the distortion characteristic.

Iref indicates the peripheral light quantity ratio caused by these factors other than the peripheral light reduction stop. When Iref is 1, the peripheral light quantity ratio does not decrease. When Iref is smaller than 1, the peripheral light quantity ratio decreases. The illuminance distribution in the image surface excluding the peripheral light reduction function is preferably close to uniform. Iref is preferably close to 1. It is preferable that Iref is at least larger than the lower limit value of the Conditional Expression (3).

When the value is smaller than the lower limit value of the Conditional Expression (3), the value is not preferable because the periphery of the field of view is darkened even in the direction that is not influenced by the peripheral light reduction stop PRS.

The Conditional Expression (4) provides a proper range of Icut/Iref.

When Icut/Iref is 1, no peripheral light reduction function occurs. When Icut/Iref is smaller than 1, a peripheral light reduction state according to the ratio is acquired at the image height end of the first direction.

To cause the peripheral light reduction to function significantly, it is required that Icut/Iref is significantly smaller than 1, and preferably at least smaller than the upper limit value of the Conditional Expression (4).

When the value is larger than the upper limit value of the Conditional Expression (4), the value is not preferable because it cannot be said that peripheral light reduction significantly functions.

In addition, according to a preferable aspect of the present embodiment, it is preferable that an edge of the opening portion shape of the peripheral light reduction stop has a shape obtained by cutting a part of an arc of a circular shape having only on the first direction side in a straight shape.

To perform peripheral light reduction only in the ultrasonic transducer direction and perform no peripheral light reduction in the other directions, it suffices to narrow only the opening portion on the ultrasonic transducer direction side of the peripheral light reduction stop. As an example, the shape of opening portion edge may be a D-cut shape. In this case, it suffices that La in the straight opening portion satisfies the Conditional Expression (2).

In addition, according to a preferable aspect of the present embodiment, it is preferable that the image pickup optical system includes a solid-state image sensor, at least one of the peripheral light reduction stop and a mirror frame including the peripheral light reduction stop has a positioning shape that does not rotate with respect to the solid-state image sensor. A direction of the opening portion shape to reduce light on the first direction side is determined in advance on the basis of the image direction of the solid-state image sensor.

It is required to align the direction of the ultrasonic transducer with the light reduction direction. The peripheral light reduction stop preferably has a positioning shape that does not rotate with respect to the solid-state image sensor, such as a notch structure K (FIG. 1B), to remove the necessity for adjustment of the rotation direction at a time of assembly.

In addition, according to a preferable aspect of the present embodiment, it is preferable that the image pickup optical system includes a solid-state image sensor, at least one of the peripheral light reduction stop and a mirror frame including the peripheral light reduction stop has a shape rotatable for adjustment with respect to the solid-state image sensor. The rotation direction is adjustable such that light reduction is possible on the first direction side on the basis of the image direction of the solid-state image sensor.

It is required to align the direction of the ultrasonic transducer with the light reduction direction. A component that is axisymmetric and rotatable has a merit that component processing is easy. In particular, when the diameter of the endoscope is reduced, the components are miniaturized, and it is required to consider the tradeoff regarding the processing accuracy and the cost. Accordingly, when a larger merit is obtained by performing rotation adjustment in the structure of the present embodiment, a design to perform rotation adjustment is preferable.

In addition, according to a preferable aspect of the present embodiment, it is preferable that the image pickup optical system includes a solid-state image sensor. The peripheral light reduction stop is disposed between the image pickup surface of the solid-state image sensor and the aperture stop.

The solid-state image sensor serves as the criteria to determine the direction relation between the screen and the subject space. Accordingly, a component requiring direction aligning with the solid-state image sensor is preferably disposed on the side close to the solid-state image sensor, regardless of the fixed structure or the adjustable structure. The design of fixing the component without rotation adjustment has a problem of deterioration in position accuracy caused by fixing at the position distant from the solid-state image sensor. In addition, even the case of including rotation adjustment has a problem of deterioration in accuracy of rotation axis shift in a position distant from the solid-state image sensor.

according to a preferable aspect of the present embodiment, it is preferable that the transducer of the endoscope is reflected in the image pickup field of view.

In addition, an endoscope according to the present embodiment includes the endoscope image pickup optical system described above. In this manner, it is possible to provide an endoscope including an endoscope optical system having a fixed-structure image (in-field structure image), such as an ultrasonic transducer image, in the optical image, achieving reduction in diameter, and reducing brightness saturation of the fixed-structure image.

Further, in addition, an endoscope according to the present embodiment includes the endoscope image pickup optical system described above. In this manner, it is possible to provide an endoscope including an endoscope optical system having a fixed-structure image (in-field structure image), such as an ultrasonic transducer image, in the optical image, achieving reduction in diameter, and reducing brightness saturation of the fixed-structure image.

Examples of the endoscope optical system will be explained hereinafter in detail on the basis of the drawings. The present disclosure is not limited to the Examples.

The Examples will be explained hereinafter. All the Examples of the endoscope optical system are supposed to be ultrasonic endoscopes for bronchi, with priority given to reduction in diameter over the image quality of the optical image.

In the following explanation, the lens cross-sectional views in Examples 1, 2, and 3 illustrate the on-axis images, the maximum image heights (IH), and rays reaching the vertical image height (IHv). Examples 1, 2, and 3 are suitable for the endoscope apparatus according to Embodiment A described above.

The lens cross-sectional views in Examples 4 and 5 illustrate the on-axis images and rays reaching the maximum image height (IH, equal to the vertical image height IHv). Examples 4 and 5 are suitable for the endoscope apparatus according to Embodiment B described above.

Example 1

Figure 2A:
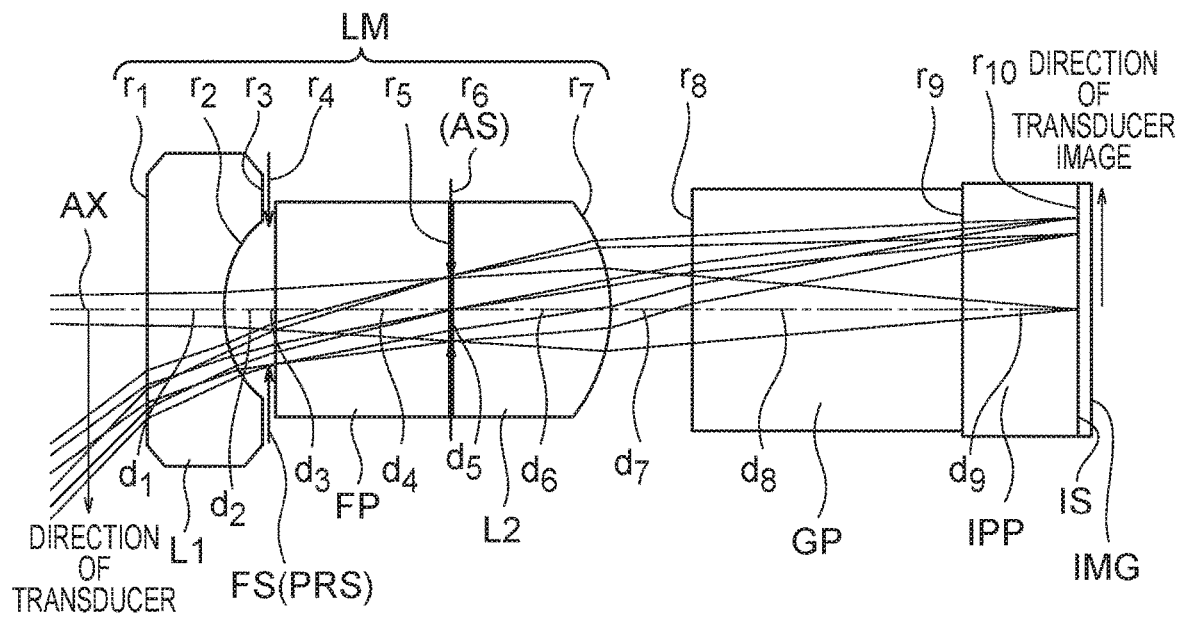
FIG. 2A is a lens cross-sectional view of an endoscope image pickup optical system according to Example 1.
Figure 2B:
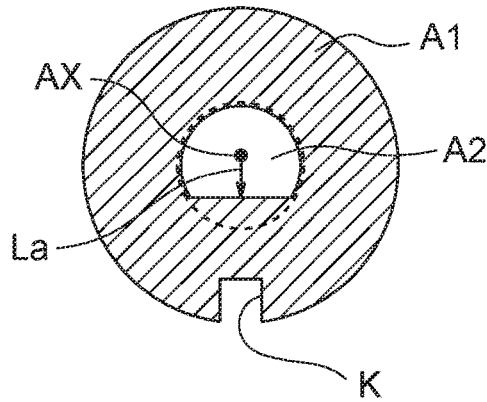
FIG. 2B is a front view of a peripheral light reduction stop according to Example 1.
Figure 2C:
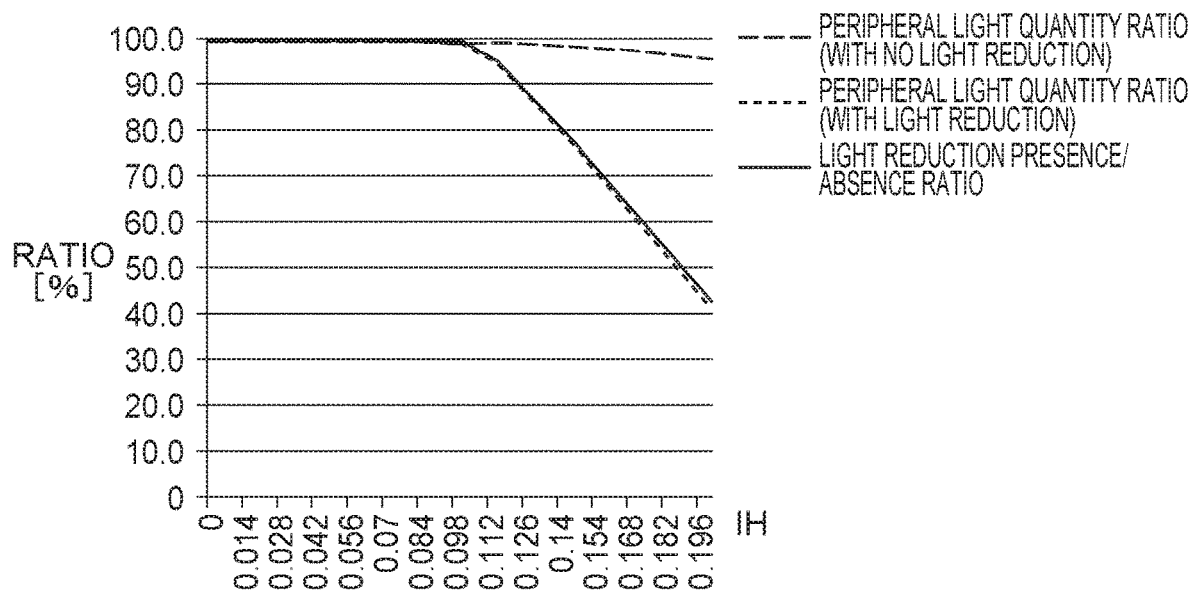
FIG. 2C is a diagram illustrating a peripheral light quantity ratio according to Example 1.

FIG. 2A is a lens cross-sectional view of an endoscope image pickup optical system according to Example 1, FIG. 2B is a front view of a peripheral light reduction stop according to Example 1, and FIG. 2C is a diagram illustrating a peripheral light quantity ratio according to Example 1. LM denotes a lens module.

An endoscope image pickup optical system OP1 according to Example 1 includes, in order from the object side, a plano-concave negative lens L1 including a concave surface opposed to the image side, a flare stop FS (peripheral light reduction stop PRS), a filter plate FP, an aperture stop AS, and a plano-convex positive lens L2 including a convex surface opposed as the image surface. In addition, on the image side, the endoscope image pickup optical system OP1 includes a frame fixing optical plate GP, an image sensor sealing optical plate IPP, and an image sensor IMG. The frame fixing optical plate GP and the image sensor sealing optical plate IPP are cemented to each other.

The present example is a greatly miniaturized (image height IH=0.242) structure to be mounted on the distal end of the endoscope. The external diameter of the plano-concave negative lens L1 having the largest diameter is φ0.8 mm.

The flare stop FS (peripheral light reduction stop PRS) formed of a thin plate having a thickness of 0.03 mm is disposed between the plano-concave negative lens L1 and the filter plate FP. The value of |Hch/Haxm|" in the object side surface of the flare stop FS (peripheral light reduction stop PRS) is 1.97.

FIG. 2B is a front view of the flare stop FS (peripheral light reduction stop PRS). The flare stop FS includes a hatched light shield portion A1 and an opening portion A2. The opening portion A2 is cut in a straight shape on the ultrasonic transducer 7 side. As described above, the flare stop FS is provided with a D-cut opening portion shape to be provided with a peripheral light reduction function, and the luminous flux made incident from the ultrasonic transducer direction side is selectively subjected to peripheral light reduction with the D-cut straight portion.

The opening size of the flare stop FS (peripheral light reduction stop PRS) is φ0.3 mm in the circular portion, and 0.095 mm (La) in the D-cut straight portion from the optical axis AX.

The peripheral light quantity ratio of the ultrasonic transducer direction in the vertical image height (IHv=0.196 mm) is:

Iref=0.958, Icut=0.410, Icut/Iref=0.428, the peripheral light reduction start image height is 0.098 mm, and the ratio of the length of the light reduction range to the vertical image size is 25% [(IHv−0.098)/(2×IHv)].

FIG. 2C is a diagram illustrating the peripheral light quantity ratio of the present example. The broken line indicates a ratio (Iref) of the peripheral light quantity to the central light quantity in the image height of the first direction in the case where the luminous flux is not shielded with the peripheral light reduction stop, the dotted line indicates a ratio (Icut) of the peripheral light quantity to the central light quantity in the image height of the first direction in the case where the luminous flux is shielded with the peripheral light reduction stop, and the solid line indicates a ratio of Icut to Iref.

When the ratio of the length of the light reduction range is large in comparison with the ratio of reflection of the ultrasonic transducer to the screen size in the vertical direction, it is possible to provide the light reduction characteristic to the whole ultrasonic transducer image.

Because the flare stop FS includes a relatively large circular opening portion in directions other than the direction of the ultrasonic transducer 7, the directions receive no peripheral light reduction function. However, because it is possible to cut unnecessary light of the flat surface portion outside the concave surface of the plano-concave negative lens L1, it is possible to maintain the function of the flare stop FS.

As described above, by forming the opening portion of the flare stop FS in a D-cut shape, the flare stop FS can also function as the peripheral light reduction stop PRS, while the function of the flare stop FS is maintained. This structure has a merit that both the flare stop function and the peripheral light reduction function are achieved only with a stop member.

Example 2

Figure 3A:
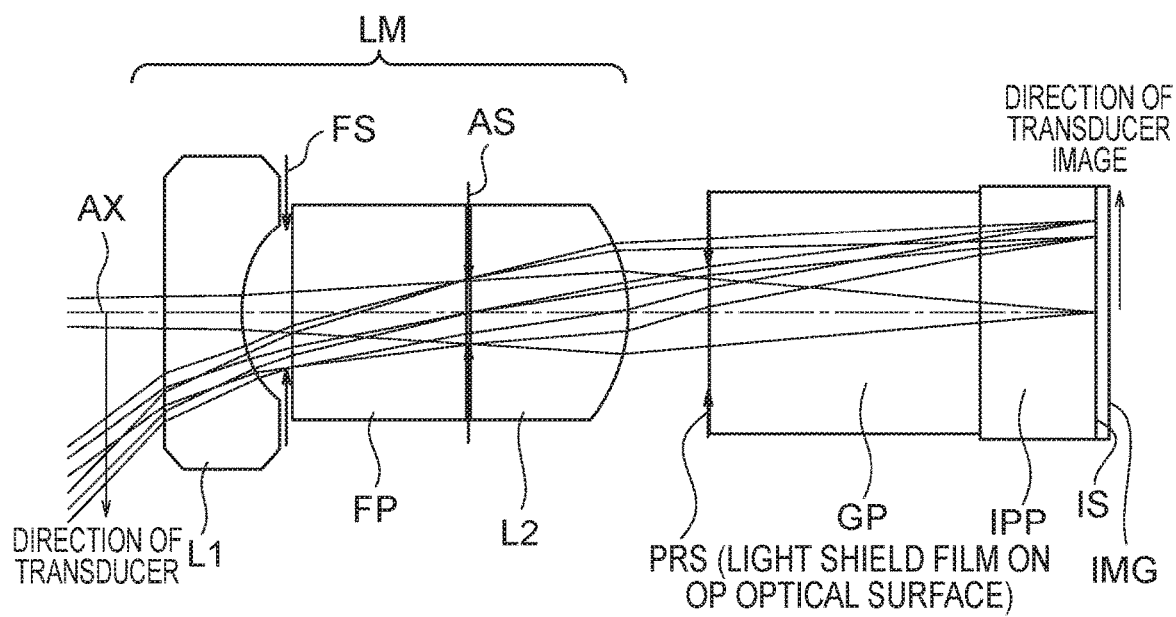
FIG. 3A is a lens cross-sectional view of an endoscope image pickup optical system according to Example 2.
Figure 3B:
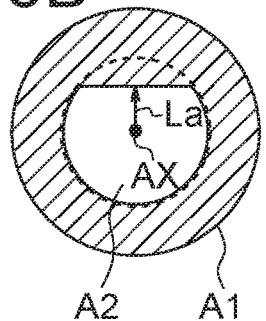
FIG. 3B and FIG. 3C are front views of a peripheral light reduction stop according to Example 2.
Figure 3C:
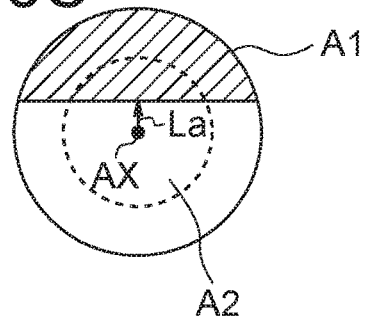
Figure 3D:
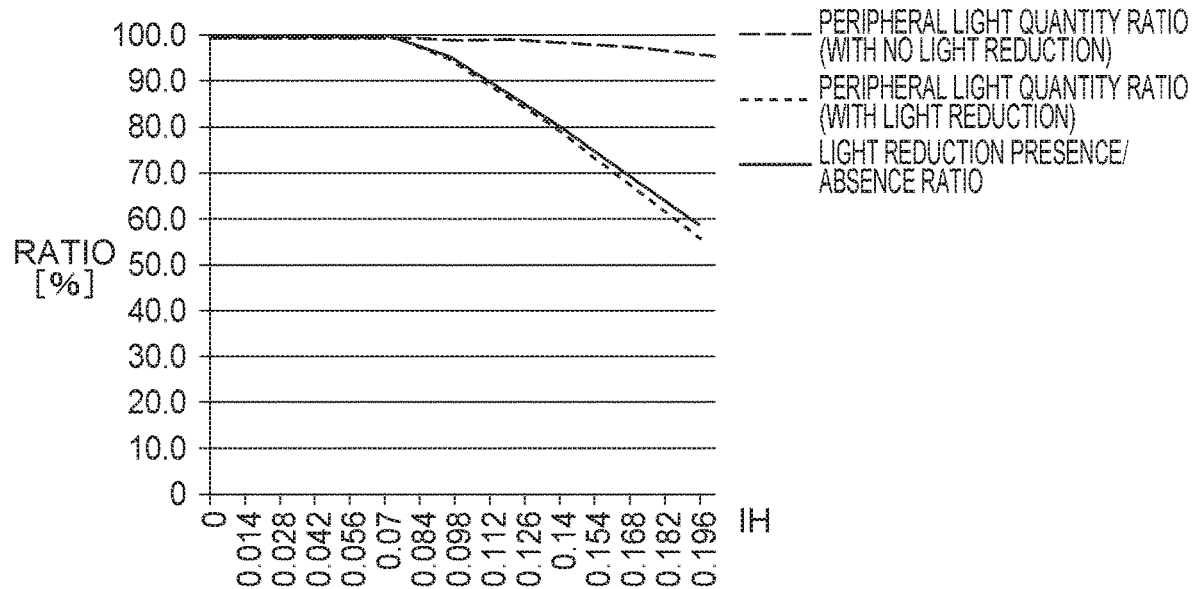
FIG. 3D is a diagram illustrating a peripheral light quantity ratio according to Example 2.

FIG. 3A is a lens cross-sectional view of an endoscope image pickup optical system according to Example 2, FIGS. 3B and 3C are a front view of a peripheral light reduction stop according to Example 2, and FIG. 3D is a diagram illustrating a peripheral light quantity ratio according to Example 2. LM denotes a lens module.

The lens cross-sectional structure of the present example is basically the same as the lens cross-sectional structure of Example 1 described above. In the present example, the peripheral light reduction stop PRS is different from that of Example 1. The peripheral light reduction stop PRS is formed as a light shield film on the object side surface of the frame fixing optical plate GP.

The value of |Hch/Haxm| in the surface on which the peripheral light reduction stop PRS is formed is 1.19.

A light shield film including an opening portion is formed on the object-side surface of the member of the frame fixing optical plate GP, to function as the peripheral light reduction stop PRS. As a method for forming a light shield film with an opening portion on the optical surface, it is possible to adopt a method of forming a light shield film by chromium vapor deposition and thereafter forming an opening portion by photoetching. As another example, it is possible to directly form the light shield portion by a precision printing technique, such as inkjet printing. The peripheral light reduction stop PRS may be manufactured as a thin plate stop member serving as a member separated from the frame fixing optical plate GP, and cemented to the object side surface of the frame fixing optical plate GP.

The present embodiment illustrates two types of structures, that is, a structure in which the opening portion shape of the peripheral light reduction stop PRS is a D-cut shape as illustrated in FIG. 3B, and a structure in which the opening portion shape is an arc shape as illustrated in FIG. 3C. The structure of FIG. 3B is a structure including a ring shape cutting function for the external diameter end side unnecessary light of the frame fixing optical plate GP, and the structure of FIG. 3C is a structure including no cutting function for the external diameter end side unnecessary light.

In the case where the peripheral light reduction stop PRS is provided with the D-cut opening portion shape, the luminous flux made incident from the ultrasonic transducer direction side is selectively subjected to peripheral light reduction with the D-cut straight portion, in the same manner as Example 1. Because the stop includes a relatively large circular opening portion in directions other than the direction of the ultrasonic transducer, the directions receive no peripheral light reduction function. The light shield portion outside the circular opening portion mainly contributes to cutting of unnecessary light on the image side beyond the aperture stop AS. For example, unnecessary light is reflected light and/or scattered light from the lens and/or the image sensor.

The circular opening size of the flare stop FS is φ0.3 mm in the circular portion.

The D-cut portion or the arc straight portion of the peripheral light reduction stop PRS has a distance of 0.115 mm (La) from the optical axis.

The peripheral light quantity ratio of the transducer direction in the vertical image height (IHv=0.196 mm) is:

Iref=0.958, Icut=0.559, Icut/Iref=0.583, the peripheral light reduction start image height is 0.07 mm, and the ratio of the length of the light reduction range to the vertical image size is 32% [(IHv−0.07)/(2×IHv)].

In the present example, Icut/Iref is set larger than that of Example 1, and the light reduction degree is set smaller than that of Example 1.

FIG. 3D is a diagram illustrating the peripheral light quantity ratio of the present example. The broken line indicates a ratio (Iref) of the peripheral light quantity to the central light quantity in the image height of the first direction in the case where the luminous flux is not shielded with the peripheral light reduction stop, the dotted line indicates a ratio (Icut) of the peripheral light quantity to the central light quantity in the image height of the first direction in the case where the luminous flux is shielded with the peripheral light reduction stop, and the solid line indicates a ratio of Icut to Iref.

Because the light reduction range is broader than that of Example 1, it is possible to deal with the case where the ratio of reflection of the ultrasonic transducer is large. In comparison with Example 1, because the light reduction range is broad, the light reduction degree is small, and a light reduction characteristic is mild.

When the necessity for cutting unnecessary light on the image side beyond the aperture stop AS is low, it is desirable to form the opening portion shape of the peripheral light reduction stop PRS in an arc shape, and increase the light transmission area of the frame fixing optical plate GP in comparison with the D-cut shape. In the case of bonding the frame fixing optical plate GP with the image sensor sealing optical plate IPP with an ultraviolet curing adhesive, there is a merit that the ultraviolet ray transmission area of the frame fixing optical plate GP increases.

Example 3

Figure 4A:
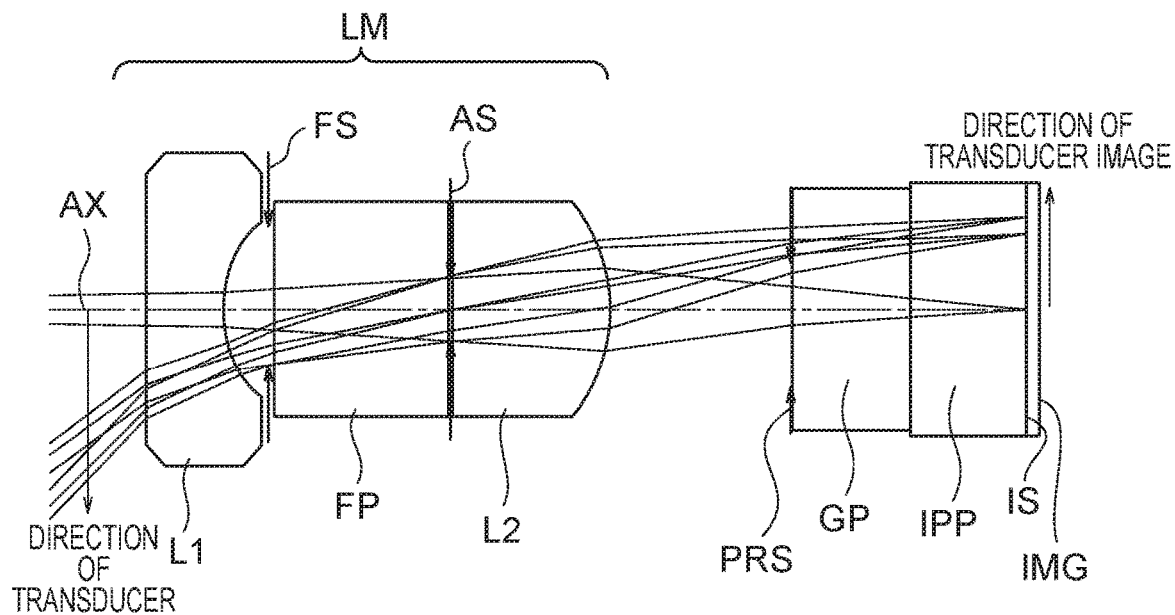
FIG. 4A is a lens cross-sectional view of an endoscope image pickup optical system according to Example 3.
Figure 4B:
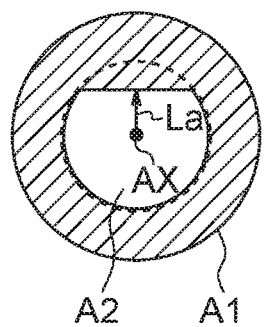
FIG. 4B is a front view of a peripheral light reduction stop according to Example 3.
Figure 4C:
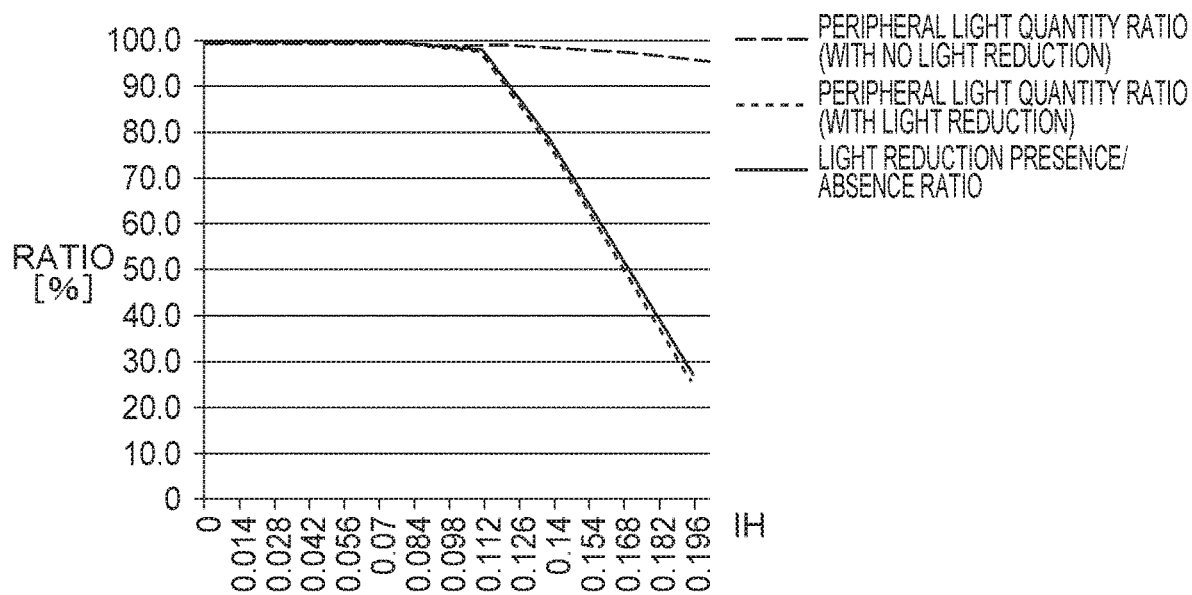
FIG. 4C is a diagram illustrating a peripheral light quantity ratio according to Example 3.

FIG. 4A is a lens cross-sectional view of an endoscope image pickup optical system according to Example 3, FIG. 4B is a front view of a peripheral light reduction stop according to Example 3, and FIG. 4C is a diagram illustrating a peripheral light quantity ratio according to Example 3. LM denotes a lens module.

The lens cross-sectional structure of the present example is basically the same as the lens cross-sectional structure of Example 2 described above. The present example is obtained by changing the thickness of the frame fixing optical plate GP, and the air space between the plano-convex positive lens L2 and the frame fixing optical plate GP from the lens data of Examples 1 and 2.

In the same manner as Example 2, the peripheral light reduction stop PRS is disposed on the object side surface of the frame fixing optical plate GP. By changing the thickness of the frame fixing optical plate GP, the value of |Hch/Haxm| is changed from Example 2. The value of |Hch/Haxm| in Example 3 is 2.92, while the value of |Hch/Haxm| in Example 2 is 1.19.

The opening size of the flare stop FS is φ0.3 mm in the circular portion.

The D-cut portion of the peripheral light reduction stop PRS has a distance of 0.12 mm (La) from the optical axis AX.

The peripheral light quantity ratio of the ultrasonic transducer direction in the vertical image height (IHv=0.196 mm) is:

Iref=0.953, Icut=0.258, Icut/Iref=0.271. Icut/Iref is smaller than those of Examples 1 and 2, and the light reduction degree is increased.

The peripheral light reduction start image height is 0.098 mm, and the ratio of the length of the light reduction range to the vertical image size is 25% [(IHv−0.098)/(2×IHv)].

FIG. 4C is a diagram illustrating the peripheral light quantity ratio of the present example. The broken line indicates a ratio (Iref) of the peripheral light quantity to the central light quantity in the image height of the first direction in the case where the luminous flux is not shielded with the peripheral light reduction stop, the dotted line indicates a ratio (Icut) of the peripheral light quantity to the central light quantity in the image height of the first direction in the case where the luminous flux is shielded with the peripheral light reduction stop, and the solid line indicates a ratio of Icut to Iref.

Although the light reduction range is the same as that of Example 1, the light reduction degree is large, and the light reduction characteristic is sharper than that of Example 1. As described above, according to the present example, it is possible to change |Hch/Haxm| only by changing the optical surface space, while substantially the same structural state is maintained, as in Examples 2 and 3. Accordingly, it is possible to achieve a more optimum design for the light reduction distribution within the range of the Conditional Expression (1).

Example 4

Figure 5A:
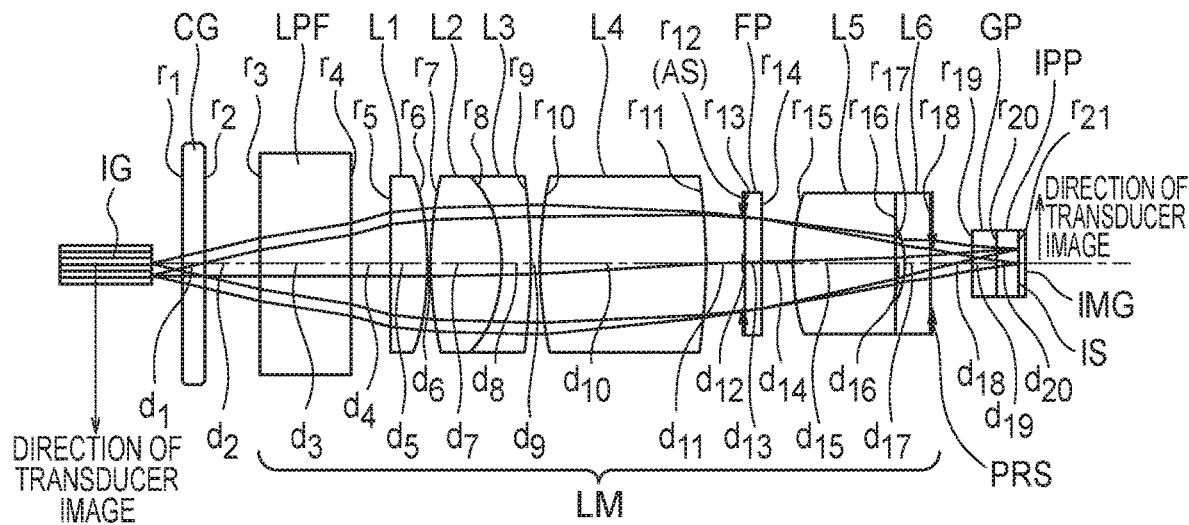
FIG. 5A is a lens cross-sectional view of an endoscope image pickup optical system according to Example 4.
Figure 5B:
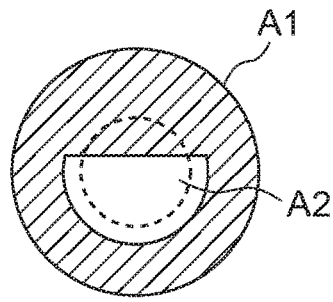
FIG. 5B is a front view of a peripheral light reduction stop according to Example 4.
Figure 5C:
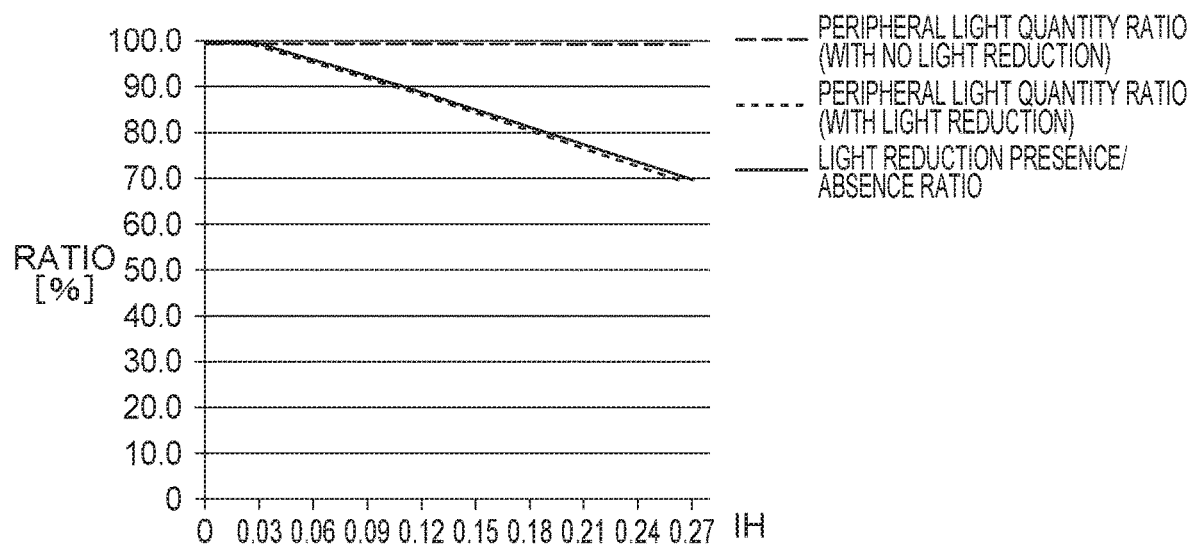
FIG. 5C is a diagram illustrating a peripheral light quantity ratio according to Example 4.

FIG. 5A is a lens cross-sectional view of an endoscope image pickup optical system according to Example 4, FIG. 5B is a front view of a peripheral light reduction stop according to Example 4, and FIG. 5C is a diagram illustrating a peripheral light quantity ratio according to Example 4. LM denotes a lens module.

The present example includes, in order from the object side, an image guide fiber IG, a cover glass CG, a low pass filter LPF, a plano-convex positive lens L1 including a convex surface opposed to the image side, a biconvex positive lens L2, a negative meniscus lens L3 including a convex surface opposed to the image side, a biconvex positive lens L4, an aperture stop AS, a filter plate FP, a plano-convex positive lens L5 including a convex surface opposed to the object side, a plano-concave negative lens L6 including a concave surface opposed to the object side, and a peripheral light reduction stop PRS. In addition, the present example includes a frame fixing optical plate GP, an image sensor sealing optical plate IPP, and a solid-state image sensor IMG.

In the structure, the biconvex positive lens L2 and the negative meniscus lens L3 are cemented to each other.

Because the present example is an image pickup optical system mounted on the operating part of the endoscope, and is not involved in reduction in diameter of the insertion part, the present example is an optical system larger than Example A. The external diameter of the cover glass CG is ϕ0.4 mm.

With the image guide fiber IG, the present example is an optical system relaying the image guide fiber IG end surface image to the image sensor IMG. The paraxial lateral magnification is −1.18. The image guide fiber IG side is telecentric, and the optical system has no concept of an angle of view, unlike the objective optical system.

Because moire occurs due to the fiber lattice structure period of the image guide fiber IG and pixels of the image sensor IMG, the optical system includes the optical low pass filter LPF.

In the present example, the optical surfaces satisfying the Conditional Expression (1) are both surfaces of the cover glass CG on the image guide fiber IG side, the last surface of the lens module LM on the image side, or both surfaces of the frame fixing optical plate GP.

In the present example, the peripheral light reduction stop PRS is disposed on the last surface of the lens module LM. The value of |Hch/Haxm| in the surface is 0.52. Because the value of |Hch/Haxm| is relatively small, a mild light reduction distribution is generated.

The D-cut portion of the peripheral light reduction stop PRS has a distance of 0.29 mm (La) from the optical axis AX.

The peripheral light quantity ratio of the ultrasonic transducer direction in the vertical image height (IHv=0.27 mm) is:

Iref=0.991, Icut=0.691, Icut/Iref=0.697. Icut/Iref is the largest in the examples of the present application, and the light reduction degree is relatively small.

The peripheral light reduction start image height is 0.02 mm, and
the ratio of the length of the light reduction range to the vertical image size is 46% [(IHv−0.02)/(2×IHv)].

FIG. 5C is a diagram illustrating the peripheral light quantity ratio of the present example. The broken line indicates a ratio (Iref) of the peripheral light quantity to the central light quantity in the image height of the first direction in the case where the luminous flux is not shielded with the peripheral light reduction stop, the dotted line indicates a ratio (Icut) of the peripheral light quantity to the central light quantity in the image height of the first direction in the case where the luminous flux is shielded with the peripheral light reduction stop, and the solid line indicates a ratio of Icut to Iref.

The light reduction range is the broadest in the examples of the present application. Also, with the small light reduction degree, the present example has the mildest light reduction characteristic in the examples of the present application.

Example 5

Figure 6A:
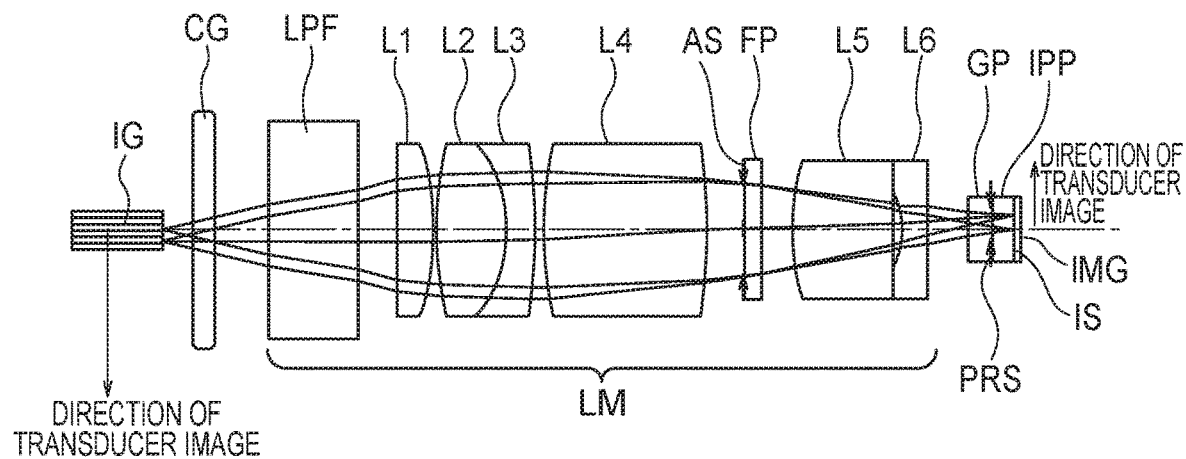
FIG. 6A is a lens cross-sectional view of an endoscope image pickup optical system according to Example 5.
Figure 6B:
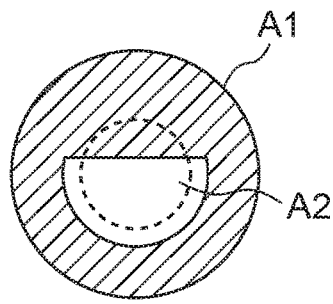
FIG. 6B is a front view of a peripheral light reduction stop according to Example 5.
Figure 6C:
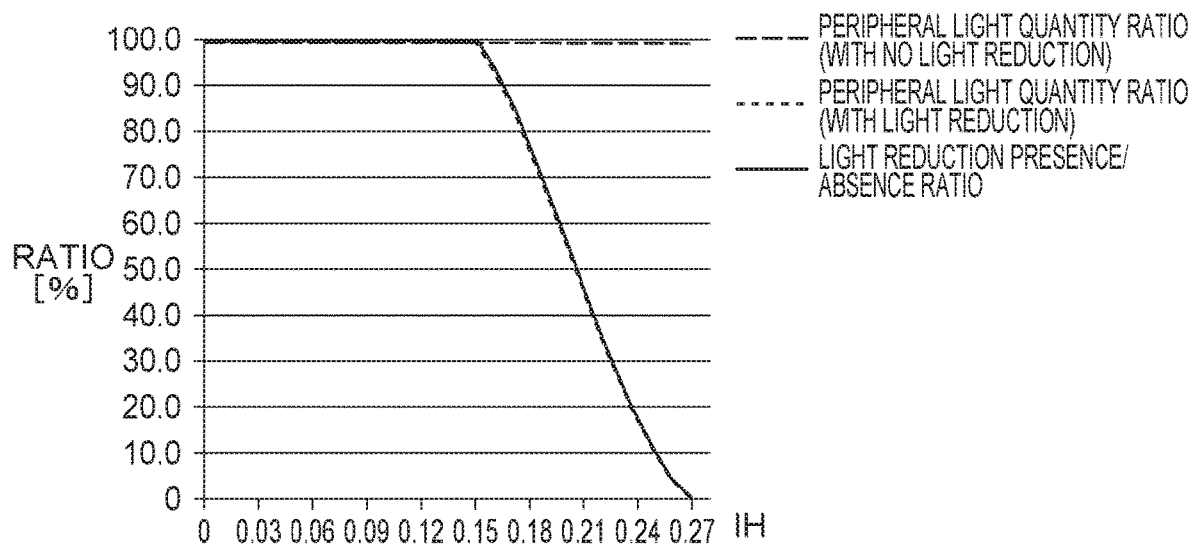
FIG. 6C is a diagram illustrating a peripheral light quantity ratio according to Example 5.

FIG. 6A is a lens cross-sectional view of an endoscope image pickup optical system according to Example 5, FIG. 6B is a front view of a peripheral light reduction stop according to Example 5, and FIG. 6C is a diagram illustrating a peripheral light quantity ratio according to Example 5. LM denotes a lens module.

The lens cross-sectional structure of the present example is basically the same as the lens cross-sectional structure of Example 4 described above.

The structure is obtained by changing the peripheral light reduction stop PRS to the image side surface of the frame fixing optical plate GP, with the same lens data as that of Example 4. The value of |Hch/Haxm| in the surface is 4.58. Because the value of |Hch/Haxm| is relatively large, a relatively sharp light reduction distribution is generated.

The D-cut portion of the peripheral light reduction stop PRS has a distance of 0.19 mm (La) from the optical axis AX.

The peripheral light quantity ratio of the ultrasonic transducer direction in the vertical image height (IHv=0.27 mm) is:

Iref=0.991, Icut=0.007, Icut/Iref=0.008.

The peripheral light reduction start image height is 0.15 mm, and the ratio of the length of the light reduction range to the vertical image size is 22% [(IHv−0.15)/(2×IHv)].

The value of Icut/Iref is the smallest in the examples of the present application, and the peripheral light quantity is substantially 0 at the vertical image height end.

FIG. 6C is a diagram illustrating the peripheral light quantity ratio of the present example. The broken line indicates a ratio (Iref) of the peripheral light quantity to the central light quantity in the image height of the first direction in the case where the luminous flux is not shielded with the peripheral light reduction stop, the dotted line indicates a ratio (Icut) of the peripheral light quantity to the central light quantity in the image height of the first direction in the case where the luminous flux is shielded with the peripheral light reduction stop, and the solid line indicates a ratio of Icut to Iref.

The light reduction range is the narrowest in the examples of the present application. Also, with the large light reduction degree, the present example has the sharpest light reduction characteristic in the examples.

Numerical data of the examples described above will be illustrated hereinafter. The symbol r denotes the radius of curvature of the surface, d denotes the thickness or the air space of the optical member, ne denotes a refractive index of the optical member with respect to the e-line, ve denotes an Abbe number of the optical member with respect to the e-line, ft denotes the focal length of the whole system of the endoscope objective optical system, FNO. denotes an F number, D0 denotes an object distance, IH denotes the maximum image height, IHv denotes the image height in the vertical direction, ω denotes the half angle of view of the maximum image height direction, and β denotes the paraxial lateral magnification. The unit of r, d, ft, D0, IH, and IHv is mm. The unit of ω is ° (degree). The circular symbol indicates that the Conditional Expression (1) is satisfied.

Example 1 and Example 2

| Surface data | | | | | | | |
|---|---|---|---|---|---|---|---|
| Surface no. | r | d | ne | ve | Haxm | Hch | |Hch/Haxm| |
| 1 | ∞ | 0.20 | 1.76820 | 70.28 | 0.0379 | −0.1972 | 5.20 |
| 2 | 0.300 | 0.10 | | | 0.0386 | −0.1185 | 3.07 |
| 3 | ∞ | 0.03 | | | 0.0490 | −0.0964 | 1.97 |
| 4 | ∞ | 0.45 | 1.51500 | 73.57 | 0.0522 | −0.0877 | 1.68 |
| 5 | ∞ | 0.01 | | | 0.0839 | −0.0029 | 0.03 |
| 6(AS) | ∞ | 0.41 | 1.88815 | 40.52 | 0.0850 | 0 | 0 |
| 7 | −0.427 | 0.21 | | | 0.1074 | 0.0609 | 0.57 |
| 8 | ∞ | 0.70 | 1.51825 | 63.93 | 0.0791 | 0.0943 | 1.19 |
| 9 | ∞ | 0.30 | 1.51825 | 63.93 | 0.0210 | 0.1655 | 7.89 |
| 10(IS) | ∞ | | | | | | |

Please note that following surface satisfied the Conditional Expression (1);
Surfaces 2, 3(example 1), 4, 7 and 8(example 2).

| Various data | |
|---|---|
| ft | 0.333 |
| FNO. | 4.24 |
| D0 | 6.5 |
| IH | 0.242 |
| IHv | 0.196 |
| 2ω | 91.3 |

Example 3

| Surface data | | | | | | | |
|---|---|---|---|---|---|---|---|
| Surface no. | r | d | ne | ve | Haxm | Hch | |Hch/Haxm| |
| 1 | ∞ | 0.20 | 1.76820 | 70.28 | 0.0379 | −0.1972 | 5.20 |
| 2 | 0.300 | 0.10 | | | 0.0386 | −0.1185 | 3.07 |
| 3 | ∞ | 0.03 | | | 0.0490 | −0.0964 | 1.97 |
| 4 | ∞ | 0.45 | 1.51500 | 73.57 | 0.0522 | −0.0877 | 1.68 |
| 5 | ∞ | 0.01 | | | 0.0839 | −0.0029 | 0.03 |
| 6(AS) | ∞ | 0.41 | 1.88815 | 40.52 | 0.0850 | 0 | 0 |
| 7 | −0.427 | 0.47 | | | 0.1074 | 0.0610 | 0.57 |
| 8 | ∞ | 0.30 | 1.51825 | 63.93 | 0.0462 | 0.1349 | 2.92 |
| 9 | ∞ | 0.30 | 1.51825 | 63.93 | 0.0210 | 0.1655 | 7.89 |
| 10(IS) | ∞ | | | | | | |

Please note that following surface satisfied the Conditional Expression (1);
Surfaces 2, 3, 4, 7 and 8(example 3).

| Various data | |
|---|---|
| ft | 0.333 |
| FNO. | 4.24 |
| D0 | 6.5 |
| IH | 0.242 |
| IHv | 0.196 |
| 2ω | 91.3 |

Example 4 and Example 5

| Surface data | | | | | | | |
|---|---|---|---|---|---|---|---|
| Surface no. | r | d | ne | ve | Haxm | Hch | |Hch/Haxm| |
| 1 | ∞ | 0.40 | 1.51825 | 63.93 | 0.1553 | −0.2299 | 1.48 |
| 2 | ∞ | 1.00 | | | 0.2223 | −0.2299 | 1.03 |

-continued

| | | | | | | | |
|---|---|---|---|---|---|---|---|
| 3 | ∞ | 1.68 | 1.55098 | 45.49 | 0.4812 | −0.2297 | 0.48 |
| 4 | ∞ | 0.70 | | | 0.7563 | −0.2296 | 0.30 |
| 5 | ∞ | 0.65 | 1.88815 | 40.52 | 0.9376 | −0.2295 | 0.24 |
| 6 | −5.470 | 0.08 | | | 1.0120 | −0.2294 | 0.23 |
| 7 | 7.242 | 1.30 | 1.59143 | 60.88 | 1.0334 | −0.2261 | 0.22 |
| 8 | −2.526 | 0.50 | 1.85504 | 23.59 | 1.0335 | −0.1808 | 0.17 |
| 9 | −11.281 | 0.18 | | | 1.0757 | −0.1707 | 0.16 |
| 10 | 7.543 | 3.06 | 1.73234 | 54.45 | 1.0865 | −0.1616 | 0.15 |
| 11 | −7.543 | 0.65 | | | 0.9661 | −0.0457 | 0.05 |
| 12(AS) | ∞ | 0.03 | | | 0.8450 | 0 | 0 |
| 13 | ∞ | 0.30 | 1.52300 | 66.30 | 0.8399 | 0.0021 | 0.00 |
| 14 | ∞ | 0.56 | | | 0.8066 | 0.0159 | 0.02 |
| 15 | 3.853 | 1.90 | 1.88815 | 40.52 | 0.7005 | 0.0553 | 0.08 |
| 16 | ∞ | 0.13 | | | 0.3755 | 0.1129 | 0.30 |
| 17 | −2.762 | 0.50 | 1.88815 | 40.52 | 0.3374 | 0.1202 | 0.36 |
| 18 | ∞ | 0.73 | | | 0.2779 | 0.1458 | 0.52 |
| 19 | ∞ | 0.45 | 1.51825 | 63.93 | 0.1176 | 0.2162 | 1.84 |
| 20 | ∞ | 0.40 | 1.51825 | 63.93 | 0.0534 | 0.2447 | 4.58 5 |
| 21(IS) | ∞ | | | | | | |

Please note that following surface satisfied the Conditional Expression (1);
Surfaces 1, 2, 18(example 4), 19, 20(example 5)

Various data

| | |
|---|---|
| ft | 2.39 |
| FNO. | 2.354 |
| D0 | 0.6 |
| IH | 0.27 |
| IHv | 0.27 |
| β | −1.18 |

Values of each of the Examples corresponding to the Conditional Expressions will be illustrated hereinafter.

| Example No. | 1 | 2 | 3 | 4 | 5 |
|---|---|---|---|---|---|
| Hch | −0.0964 | 0.0943 | 0.1349 | 0.1458 | 0.2447 |
| Haxm | 0.0490 | 0.0791 | 0.0462 | 0.2779 | 0.0534 |
| La | 0.095 | 0.115 | 0.120 | 0.290 | 0.190 |
| \|Hch/Haxm\| | 1.97 | 1.19 | 2.92 | 0.52 | 4.58 |
| (La − \|Hch\|)/ \|Haxm\| | −0.03 | 0.26 | −0.32 | 0.52 | −1.02 |
| Iref | 0.958 | 0.958 | 0.953 | 0.991 | 0.991 |
| Icut | 0.410 | 0.559 | 0.258 | 0.691 | 0.007 |
| Icut/Iref | 0.428 | 0.583 | 0.271 | 0.697 | 0.008 |

Figure 10:
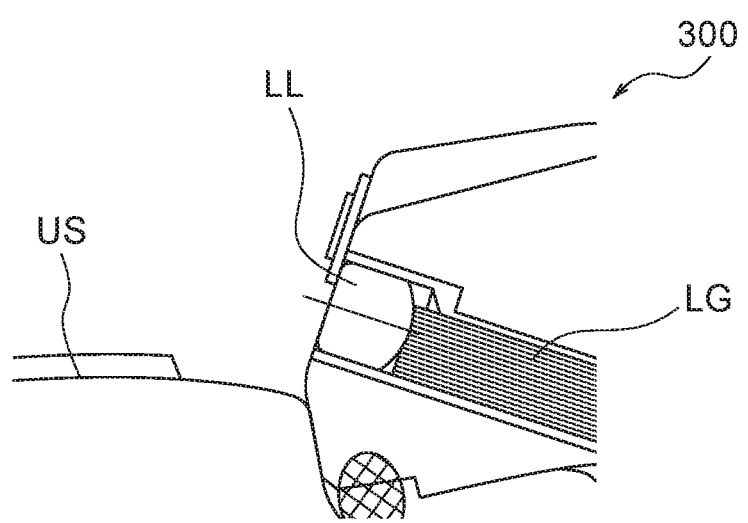
FIG. 10 is a diagram illustrating a structure of an illumination lens at a distal end part of an ultrasonic endoscope.

FIG. 10 is a diagram illustrating a structure of the illumination lens at a distal end part of an ultrasonic endoscope. FIG. 10 illustrates an illumination lens structure preferably to be combined with the image pickup optical system described above. In an ultrasonic endoscope 300 including the image pickup optical system according to the example, the ultrasonic transducer and the illumination lens are disposed close to each other with a distance of 2 mm or less, because of reduction in diameter and reduction in the length of the distal end part. With proximity of the illumination, the ultrasonic transducer easily has high illuminance.

The measure against saturation of brightness of the ultrasonic transducer by peripheral light reduction on the image pickup side in each of the examples does not restrict the measure against saturation of brightness on the illumination side, and it is possible to achieve both.

Examples of numerical values will be illustrated hereinafter.

As data of the illumination lens, the lens is a plano-convex lens LL, the external diameter is ϕ0.75 mm, the central thickness is 0.62 mm, the convex surface R is 0.639 mm, and ne is 1.88815.

As data of the light guide fiber LG, the effective diameter of the end surface is ϕ0.555 mm, and eccentricity with respect to the illumination lens axis is 0.07 mm (transducer side).

By causing the light guide fiber LG to be eccentric to the ultrasonic transducer US side with respect to the plano-convex lens LL (the lens located most on the object side in the illumination optical system), it is possible to reduce the illumination intensity on the ultrasonic transducer US side. In this state, the illumination emission intensity on the side (organ observation side) opposite to the ultrasonic transducer tends to increase with respect to no eccentricity.

When automatic dimming functions, with increase of the illumination intensity on the organ observation side having a large area on the screen, the endoscope light source controls light to reduce the light quantity. In addition, with decrease of the illumination intensity on the ultrasonic transducer side in the optical design, it is possible to improve brightness saturation of the ultrasonic transducer more preferably.

Various modifications are possible for the present disclosure within the range not departing from the gist thereof.

A structure requiring observation of the neighboring of the fixed structure at the distal end of the endoscope is not limited to an ultrasonic endoscope. For example, in an endoscope in which any treatment function is united with the endoscope distal end part, an image pickup optical system enabling constant visual recognition of the treatment function unit is required. In addition, in the case of providing the endoscope distal end part with a close observation optical system to be brought close to the organ and perform enlargement observation and optical measurement, an image pickup optical system enabling visual recognition of the measurement region of the close observation optical system in a bird's eye view is required separately from the proximity optical system. In either case where the fixed structure is an ultrasonic transducer, a treatment function unit, or a constituent element of a close observation optical system, the brightness saturation problem of the fixed structure image is the same, and it is possible to improve brightness saturation by using the structure of the present disclosure.

As described above, the present disclosure provides an image pickup optical system, an endoscope, and an image pickup apparatus achieving reduction in diameter and reducing brightness saturation of the fixed structure image.

According to the present disclosure, it is possible to provide an image pickup optical system, an endoscope, and an image pickup apparatus serving as or including an image pickup optical system including an in-filed structure image (fixed structure image), such as a transducer image, in the optical image, achieving reduction in diameter, and reducing brightness saturation of the in-field structure image (fixed structure image).

What is claimed is:

1. An image pickup optical system including an image pickup field of view in which part of an endoscope is reflected, the image pickup optical system comprising:
   an aperture stop; and
   a peripheral light reduction stop, wherein
   the peripheral light reduction stop is positioned in an optical axis direction satisfying the following Conditional Expression (1),
   in the peripheral light reduction stop, when a side on which the part of the endoscope exists in the image pickup field of view is a first direction and a side on which no part of the endoscope exists in the image pickup field of view is a second direction, an opening of the peripheral light reduction stop satisfies the following Conditional Expression (2), and a peripheral light reduction quantity in the second direction is smaller than a peripheral light reduction quantity in the first direction by shielding no effective luminous flux in the second direction or reducing a shielding quantity of the effective luminous flux:

$$0.5 < |Hch/Haxm| < 5 \tag{1}$$

$$-1.2 < (La - |Hch|)/|Haxm| < 0.6 \tag{2}$$

where
   Hch is a chief ray height of image height in the first direction at the position of the peripheral light reduction stop,
   Haxm is an on-axis marginal beam height at the position of the peripheral light reduction stop, and
   La is a distance from an optical axis to an opening end in the first direction of the peripheral light reduction stop.

2. The image pickup optical system according to claim 1, wherein the following Conditional Expressions (3) and (4) are satisfied:

$$0.6 < Iref \tag{3}$$

$$Icut/Iref < 0.7 \tag{4}$$

where
   Iref is a ratio of a peripheral light quantity to a central light quantity in image height of the first direction when effective luminous flux is not shielded with the peripheral light reduction stop, and
   Icut is a ratio of the peripheral light quantity to the central light quantity in the image height of the first direction when the effective luminous flux is shielded with the peripheral light reduction stop.

3. The image pickup optical system according to claim 1, wherein an edge of the opening of the peripheral light reduction stop has a shape obtained by cutting a part of an arc of a circular shape having only on the first direction side in a straight shape.

4. The image pickup optical system according to claim 1, further comprising:
   a solid-state image sensor, wherein
   at least one of the peripheral light reduction stop and a mirror frame including the peripheral light reduction stop has a positioning shape that does not rotate with respect to the solid-state image sensor, and
   a direction of the opening to reduce light on the first direction side is determined in advance, on the basis of an image direction of the solid-state image sensor.

5. The image pickup optical system according to claim 1, further comprising:
   a solid-state image sensor, wherein
   at least one of the peripheral light reduction stop and a mirror frame including the peripheral light reduction stop has a shape rotatable for adjustment with respect to the solid-state image sensor, and
   a rotation direction is adjustable such that light reduction is possible on the first direction side on the basis of an image direction of the solid-state image sensor.

6. The image pickup optical system according to claim 1, further comprising:
   a solid-state image sensor, wherein
   the peripheral light reduction stop is disposed between an image pickup surface of the solid-state image sensor and the aperture stop.

7. The image pickup optical system according to claim 1, wherein a transducer of the endoscope is reflected in the image pickup field of view.

8. An endoscope comprising an image pickup optical system, wherein
   the image pickup optical system includes an image pickup field of view in which part of the endoscope is reflected;
   the endoscope further comprising:
   an aperture stop; and
   a peripheral light reduction stop,
   the peripheral light reduction stop is positioned in an optical axis direction satisfying the following Conditional Expression (1),
   in the peripheral light reduction stop, when a side on which the part of the endoscope exists in the image pickup field of view is a first direction and a side on which no part of the endoscope exists in the image pickup field of view is a second direction,
   an opening of the peripheral light reduction stop satisfies the following Conditional Expression (2), and
   a peripheral light reduction quantity in the second direction is smaller than a peripheral light reduction quantity in the first direction by shielding no effective luminous flux in the second direction or reducing shielding quantity of the effective luminous flux:

$$0.5 < |Hch/Haxm| < 5 \tag{1}$$

$$-1.2 < (La - |Hch|)/|Haxm| < 0.6 \tag{2}$$

where
   Hch is a chief ray height of image height in the first direction at the position of the peripheral light reduction stop,
   Haxm is an on-axis marginal beam height at the position of the peripheral light reduction stop, and
   La is a distance from an optical axis to an opening end in the first direction of the peripheral light reduction stop.

9. The endoscope according to claim 8, wherein the following Conditional Expressions (3) and (4) are satisfied:

$$0.6 < Iref \quad (3)$$

$$Icut/Iref < 0.7 \quad (4)$$

where

Iref is a ratio of a peripheral light quantity to a central light quantity in image height of the first direction when effective luminous flux is not shielded with the peripheral light reduction stop, and Icut is a ratio of the peripheral light quantity to the central light quantity in the image height of the first direction when the effective luminous flux is shielded with the peripheral light reduction stop.

10. The endoscope according to claim 8, wherein an edge of the opening of the peripheral light reduction stop has a shape obtained by cutting a part of an arc of a circular shape only on the first direction side in a straight shape.

11. The endoscope according to claim 8, further comprising:
a solid-state image sensor, wherein
at least one of the peripheral light reduction stop and a mirror frame including the peripheral light reduction stop has a positioning shape that does not rotate with respect to the solid-state image sensor, and
a direction of the opening to reduce light on the first direction side is determined in advance, on the basis of an image direction of the solid-state image sensor.

12. The endoscope according to claim 8, further comprising:
a solid-state image sensor, wherein
at least one of the peripheral light reduction stop and a mirror frame including the peripheral light reduction stop has a shape rotatable for adjustment with respect to the solid-state image sensor, and
a rotation direction is adjustable such that light reduction is possible on the first direction side on the basis of an image direction of the solid-state image sensor.

13. The endoscope according to claim 8, further comprising:
a solid-state image sensor, wherein
the peripheral light reduction stop is disposed between an image pickup surface of the solid-state image sensor and the aperture stop.

14. The endoscope according to claim 8, wherein a transducer of the endoscope is reflected in the image pickup field of view.

15. An image pickup apparatus comprising:
the image pickup optical system according to claim 1; and
an image sensor.

16. The image pickup apparatus according to claim 15, wherein the following Conditional Expressions (3) and (4) are satisfied:

$$0.6 < Iref \quad (3)$$

$$Icut/Iref < 0.7 \quad (4)$$

where

Iref is a ratio of a peripheral light quantity to a central light quantity in image height of the first direction when effective luminous flux is not shielded with the peripheral light reduction stop, and Icut is a ratio of the peripheral light quantity to the central light quantity in the image height of the first direction when the effective luminous flux is shielded with the peripheral light reduction stop.

17. The image pickup apparatus according to claim 15, wherein
an edge of the opening of the peripheral light reduction stop has a shape obtained by cutting a part of an arc of a circular shape only on the first direction side in a straight shape.

18. The image pickup apparatus according to claim 15, further comprising:
a solid-state image sensor, wherein
at least one of the peripheral light reduction stop and a mirror frame including the peripheral light reduction stop has a positioning shape that does not rotate with respect to the solid-state image sensor, and
a direction of the opening to reduce light on the first direction side is determined in advance, on the basis of an image direction of the solid-state image sensor.

19. The image pickup apparatus according to claim 15, further comprising:
a solid-state image sensor, wherein
at least one of the peripheral light reduction stop and a mirror frame including the peripheral light reduction stop has a shape rotatable for adjustment with respect to the solid-state image sensor, and
a rotation direction is adjustable such that light reduction is possible on the first direction side on the basis of an image direction of the solid-state image sensor.

20. The image pickup apparatus according to claim 15, further comprising:
a solid-state image sensor, wherein
the peripheral light reduction stop is disposed between an image pickup surface of the solid-state image sensor and the aperture stop.

* * * * *